US010898100B2

(12) United States Patent
Rutkove et al.

(10) Patent No.: US 10,898,100 B2
(45) Date of Patent: Jan. 26, 2021

(54) ELECTRICAL IMPEDANCE MYOGRAPHY

(71) Applicants:Beth Israel Deaconess Medical Center, Inc., Boston, MA (US); Northeastern University, Boston, MA (US)

(72) Inventors: Seward B. Rutkove, Brookline, MA (US); Carl A. Shiffman, Waban, MA (US); Ronald Aaron, Newton Centre, MA (US)

(73) Assignees: Beth Israel Deaconess Medical Center, Inc., Boston, MA (US); Northeastern University, Boston, MA (US)

( * ) Notice: Subject to any disclaimer, the term of this patent is extended or adjusted under 35 U.S.C. 154(b) by 1047 days.

(21) Appl. No.: 14/660,855

(22) Filed: Mar. 17, 2015

(65) Prior Publication Data

US 2015/0196220 A1    Jul. 16, 2015

Related U.S. Application Data

(60) Division of application No. 13/598,109, filed on Aug. 29, 2012, now Pat. No. 9,014,797, which is a
(Continued)

(51) Int. Cl.
*A61B 5/0488* (2006.01)
*A61B 5/053* (2006.01)
*A61B 5/0492* (2006.01)

(52) U.S. Cl.
CPC .......... *A61B 5/0492* (2013.01); *A61B 5/0488* (2013.01); *A61B 5/053* (2013.01);
(Continued)

(58) Field of Classification Search
CPC ... A61B 5/0536; A61B 5/0488; A61B 5/0492; A61B 5/053; A61B 2562/046;
(Continued)

(56) References Cited

U.S. PATENT DOCUMENTS 5,272,624 A * 12/1993 Gisser .................. A61B 5/0536
600/393
5,807,251 A *  9/1998 Wang .................... A61B 5/0536
600/407
(Continued)

FOREIGN PATENT DOCUMENTS

| WO | WO 00/19892 A1 | 4/2000 |
|---|---|---|
| WO | WO 02/065900 A2 | 8/2002 |
| WO | WO 2004/049936 A2 | 6/2004 |

OTHER PUBLICATIONS

International Search Report and Written Opinion for International Application No. PCT/US2006/036863 dated Nov. 26, 2007.
(Continued)

*Primary Examiner* — Jacqueline Cheng
*Assistant Examiner* — May Abouelela
(74) *Attorney, Agent, or Firm* — Wolf, Greenfield & Sacks, P.C.

(57) ABSTRACT

Electrical impedance myography (EIM) can be used for the assessment and diagnosis of muscular disorders. EIM includes applying an electrical signal to a region of tissue and measuring a resulting signal. A characteristic of the region of tissue is determined based on the measurement. Performing EIM at different frequencies and/or different angular orientations with respect to a muscle can aid in the assessment and diagnosis. Devices are described that facilitate assessment and diagnosis using EIM.

19 Claims, 7 Drawing Sheets

Related U.S. Application Data continuation of application No. 11/992,430, filed as application No. PCT/US2006/036863 on Sep. 21, 2006, now abandoned.

(60) Provisional application No. 60/719,426, filed on Sep. 21, 2005.

(52) U.S. Cl.
CPC .......... *A61B 5/0531* (2013.01); *A61B 5/0536* (2013.01); *A61B 2562/046* (2013.01); *A61B 2562/164* (2013.01)

(58) Field of Classification Search
CPC ...... A61B 2562/0209; A61B 2018/124; A61B 5/14532; A61B 2018/00839; A61B 18/082; A61B 2018/00875; A61B 5/0531; A61N 1/0484; A61N 1/0492; G01N 27/026
USPC ................................ 600/546, 547, 300, 393
See application file for complete search history.

(56) References Cited

U.S. PATENT DOCUMENTS

| | | | | |
|---|---|---|---|---|
| 5,919,142 A * | 7/1999 | Boone | ................. | A61B 5/0522 600/547 |
| 6,122,544 A | 9/2000 | Organ | | |
| 6,134,480 A * | 10/2000 | Minogue | .............. | A61N 1/0452 600/391 |
| 6,308,096 B1 | 10/2001 | Masuo | | |
| 6,501,984 B1 * | 12/2002 | Church | ................ | A61B 5/0536 600/547 |
| 6,768,921 B2 * | 7/2004 | Organ | ................... | A61B 5/0536 600/547 |
| 6,922,586 B2 * | 7/2005 | Davies | ............... | A61B 5/04002 600/506 |
| 6,940,286 B2 * | 9/2005 | Wang | ..................... | G01N 27/20 324/450 |
| 6,970,741 B1 * | 11/2005 | Whitehurst | ............ | A61B 5/053 128/899 |
| 9,014,797 B2 | 4/2015 | Rutkove et al. | | |
| 9,974,463 B2 * | 5/2018 | Rutkove | .............. | A61B 5/4519 |
| 2003/0130711 A1 * | 7/2003 | Pearson | ............. | A61B 18/1477 607/101 |
| 2004/0054273 A1 * | 3/2004 | Finneran | ............ | A61B 5/04004 600/393 |
| 2004/0122336 A1 * | 6/2004 | Jang | ..................... | A61B 5/0531 600/547 |
| 2005/0059902 A1 * | 3/2005 | Itagaki | ................. | A61B 5/0537 600/547 |
| 2005/0113691 A1 * | 5/2005 | Liebschner | .......... | A61B 5/4504 600/437 |
| 2005/0261585 A1 * | 11/2005 | Makin | ..................... | A61B 5/01 600/439 |
| 2006/0004301 A1 | 1/2006 | Kasevich | | |
| 2006/0085049 A1 | 4/2006 | Cory et al. | | |
| 2006/0155386 A1 * | 7/2006 | Wells | ................... | A61B 5/0006 623/25 |
| 2009/0171234 A1 * | 7/2009 | Gurewitsch | ........... | A61B 5/053 600/547 |
| 2010/0292603 A1 | 11/2010 | Shiffman et al. | | |
| 2012/0245436 A1 * | 9/2012 | Rutkove | ............... | A61B 5/4519 600/301 |
| 2012/0323136 A1 | 12/2012 | Rutkove et al. | | |
| 2017/0007151 A1 | 1/2017 | Rutkove et al. | | |
| 2019/0069801 A1 | 3/2019 | Rutkove et al. | | |

OTHER PUBLICATIONS

Aaron et al., "Anisotropy of human muscle via non-invasive impedance measurements," *Phys. Med. Biol.*, 1997, pp. 1245-1262, vol. 42.

International Preliminary Report on Patentability for Application No. PCT/US2006/036863 dated Mar. 26, 2008.

* cited by examiner

ELECTRICAL IMPEDANCE MYOGRAPHY

RELATED APPLICATIONS

This application is a division of application Ser. No. 13/598,109, filed on Aug. 29, 2012, which is a continuation of application Ser. No. 11/992,430, filed on Aug. 3, 2010, which is a U.S. National Stage of PCT/US2006/036863, filed on Sep. 21, 2006, which claims priority under 35 U.S.C. § 119(e) to Provisional Application No. 60/719,426, filed on Sep. 21, 2005, all of which applications are incorporated herein by reference in their entirety.

FEDERALLY SPONSORED RESEARCH

This invention was made with government support under grant NS042037 awarded by NIH. The government has certain rights in the invention.

BACKGROUND OF INVENTION

Neuromuscular diseases encompass a large collection of disorders, ranging from relatively mild conditions such as focal compression neuropathies and nerve root injuries, to severe and life-threatening syndromes, including amyotrophic lateral sclerosis (ALS) and muscular dystrophies. These disorders may lead to muscle atrophy and weakness, caused either by injury to or disease of the neuron (neurogenic disorders), the neuromuscular junction, or the muscle cell itself (myopathic disorders). Another disorder, disuse atrophy, may occur occur when a limb is immobilized or a patient is bed-bound for a prolonged period of time, although not classically considered a neuromuscular disorder, also produces substantial morbidity.

Neuromuscular diseases have been assessed and diagnosed using various techniques, including nerve condition studies, needle electromyography, muscle imaging, muscle biopsy and genetic testing. However, the initial assessment of the neuromuscular diseases has advanced relatively little beyond conventional needle electromyography and nerve conduction techniques. Similarly, there have been few good approaches to the assessment of disuse atrophy and dysfunction.

Nerve conduction studies (NCSs) and needle electromyography (EMG) are often the first tests obtained when evaluating a patient for neuromuscular causes of atrophy. NCSs involve stimulation of a nerve with one set of electrodes and recording the resulting muscle or nerve potential with a second set of electrodes. Although useful for evaluating nerve pathology, NCSs are of limited use for evaluating muscle disease or disuse states. The stimuli can be uncomfortable and only a relatively limited set of distal muscles in the arms and legs can be evaluated.

Needle electromyography is geared more specifically to muscle evaluation. Needle electromyography can provide a quick survey of muscles to determine whether they are being affected by neurogenic injury or myopathic injury. However, the test has considerable limitations. First, needle electromyography is very subjective because physicians qualitatively assess the attributes of motor unit action potentials (MUAPs) as they rapidly pass across an oscilloscopic display. Second, there are substantial limitations with respect to the sensitivity of needle electromyography. It is a common experience amongst electromyographers that only with extensive probing are one or two questionably abnormal MUAPs identified. Third, the lack of quantifiable results makes EMG an unsuitable modality for following disease progression/remission. Finally, needle EMG remains a somewhat painful, invasive procedure and can thus only be used in a very limited fashion in children.

Imaging techniques such as magnetic resonance imaging (MRI) and ultrasound have found some use in muscle atrophy assessment. For example, MRI can be used to identify muscles with active inflammation to assist with biopsy site choice in patients with myositis. However, MRI has otherwise remained of limited use since it is difficult to evaluate different areas of the body, is costly, cannot easily assess dynamic muscle states during muscle contraction, and may not be used in patients with pacemakers and implanted defibrillators. Ultrasound has found limited use in neuromuscular disease and disuse atrophy assessment, and remains very qualitative.

Muscle biopsy is another test for evaluation of muscle disease and can be helpful in arriving at a specific diagnosis. Muscle biopsy frequently yields limited or contradictory information and may be unsuitable for monitoring progression of atrophy because of its inherent invasiveness. Given that many diseases are patchy (i.e., regions of diseased muscle tissue is interspersed throughout ostensibly healthy muscle tissue), a negative biopsy does not exclude disease, and repeat biopsies sometimes need to be performed.

Genetic tests can be very useful for assisting in the evaluation of a number of mostly rare conditions (such as the muscular dystrophies), but is expensive and not relevant to a variety of the most common, acquired conditions.

SUMMARY OF INVENTION

Existing techniques for assessing and diagnosing neuromuscular diseases can be unreliable, subjective and sometimes painful to the patient. Embodiments of the invention relate to methods and devices that can provide a reliable, quantitative and relatively painless assessment and diagnoses of neuromuscular diseases, and for assessment of disuse atrophy. Applicant has developed generally non-invasive techniques for characterizing muscle tissue, facilitating the assessment, diagnosis, monitoring and/or treatment of characteristics and/or conditions of muscle tissue that may be indicative of one or more neuromuscular disorders, including disuse atrophy.

One embodiment according to the present invention includes a method of determining at least one characteristic of a region of tissue, the method comprising acts of applying a plurality of first electrical signals to the region of tissue, each of the plurality of first electrical signals being applied at a respective one of a plurality of orientations, obtaining a plurality of measurements from the region of tissue, each of the plurality of measurements indicative of a respective one of a plurality of second electrical signals, each of the plurality of second electrical signals resulting from applying a respective one of the plurality of first electrical signals, and determining the at least one characteristic based, at least in part, on the plurality of measurements.

Another embodiment according to the present invention includes a method of determining at least one characteristic of a region of tissue, the method comprising acts of applying a plurality of first electrical signals to the region of tissue, each of the plurality of first electrical signals being applied at a respective one of a plurality of frequencies, obtaining a plurality of measurements from the region of tissue, each of the plurality of measurements indicative of a respective one of a plurality of second electrical signals, each of the plurality of second electrical signals resulting from applying a respective one of the plurality of first electrical signals, and determining the at least one characteristic based, at least in part, on the plurality of measurements.

Another embodiment according to the present invention includes a device adapted for application to a surface of skin to determine at least one characteristic of a region of tissue, the device comprising a first electrode adapted to apply a first electrical signal to the region of tissue, a second electrode adapted to detect a second electrical signal at the region of tissue resulting from the application of the first electrical signal, a rotatable base on which the first electrode and the second electrode are mounted and arranged such that, when the rotatable base is rotated, the first electrode and the second electrode are rotated with respect to the region of tissue to apply the first electrical signal to the region of tissue at a plurality of orientations and to detect the second electrical signal resulting from the application of the first electrical signal at the plurality of orientations, and a measurement component coupled to the second electrode to obtain at least one measurement indicative of the second electrical signal at each of the plurality of orientations.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Embodiments of the invention relate to methods and devices for determining a characteristic of a region of tissue by applying an electrical signal to the region and, in response to applying the electrical signal, obtaining an electrical measurement of the region of tissue. Such a technique may be referred to as electrical impedance myography (EIM). Neuromuscular disorders can be assessed and diagnosed based on the measured electrical signals. In some embodiments, the quantitative nature of the techniques described herein can facilitate the evaluation of the progress of a neuromuscular disorder. For example, the effectiveness of treatments for neuromuscular disorders, such as newly-developed drugs, may be evaluated using the techniques described herein.

To perform an EIM technique, an electrical signal (e.g., electric current) may be applied to the region of tissue using electrodes applied to the skin. Various characteristics can be determined based on the electrical parameters that are measured for the region, such as the impedance, reactance, resistance and/or phase shift. In contrast to existing techniques for assessing and diagnosing neuromuscular disease, EIM may be more rapid, more quantitative, less invasive and more repeatable. EIM can be used for the assessment of muscle conditions, and more specifically, neuromuscular disease. However, it should be appreciated that EIM is not limited to the assessment of neuromuscular disease, as any other suitable tissue characteristic(s) may be measured using EIM, such as the amount of muscle atrophy that has occurred through disuse of a muscle (or more rarely, hypertrophy), as the aspects of the invention are not limited in this respect.

Some embodiments of the invention relate to methods and devices for performing multi-frequency EIM, which involves performing EIM using at least two different frequencies of electrical signals. Because the electrical parameters of a muscle can be dependent on the frequency of an alternating current applied to a muscle, measurements of the muscle impedance for a plurality of frequencies can be utilized to facilitate diagnosis of muscle condition, and to differentiate between normal and abnormal muscle tissue. Multi-frequency EIM can be performed by varying the frequency of the alternating current applied to the muscle or group of muscles. For example, the frequency that is applied may be in the range between about 2 kHz and about 2 MHz, but the invention is not limited to this particular frequency range, as any other suitable frequency range can be used.

The alternating current can be injected via one set of surface electrodes (referred to as current-injecting electrodes), and the resulting voltage patterns can be recorded via a second set of surface electrodes (referred to as voltage-recording electrodes). Based on the measurement of the injected current's magnitude, an impedance instrument can convert the voltage signals into a resistance (R) and reactance (X), for each applied frequency. From these parameters, a phase ($\theta$) may be computed, for each applied frequency. However, any suitable electrical parameters may be measured and/or calculated for evaluation of muscle tissue, as the invention is not limited in this respect.

Some embodiments of the invention relate to a method and apparatus for performing multidirectional EIM (also referred to as rotational EIM). Because the measured electrical parameters of a muscle can be anisotropic, and therefore dependent on the orientation of the measurement electrodes relative to the muscle fibers, electrical parameter measurements in a plurality of different directions can be utilized to facilitate diagnosis of muscle condition, and to differentiate between normal and abnormal muscle tissue.

In some embodiments of the invention, a method and apparatus is provided for both multi-frequency and multidirectional EIM. Such combined measurements can provide more diagnostic information than multi-frequency or multidirectional EIM alone. In some embodiments, a method and apparatus is provided for performing EIM during contraction of a muscle, referred to as dynamic EIM. The contraction can be voluntary or electrically induced. In yet other embodiments, a combination of multi-frequency, multidirectional, and/or dynamic EIM measurements can also be used to differentiate between different types of abnormal muscle conditions, including neuromuscular conditions (e.g., amyotrophic lateral sclerosis (ALS), inflammatory myopathy) and neurogenic conditions. It should be appreciated that any of the aforementioned embodiments can be performed on one or more muscles including quadriceps, biceps, tibialis anterior, etc., as the invention is not limited to any specific muscle or muscle group.

Figure 1:
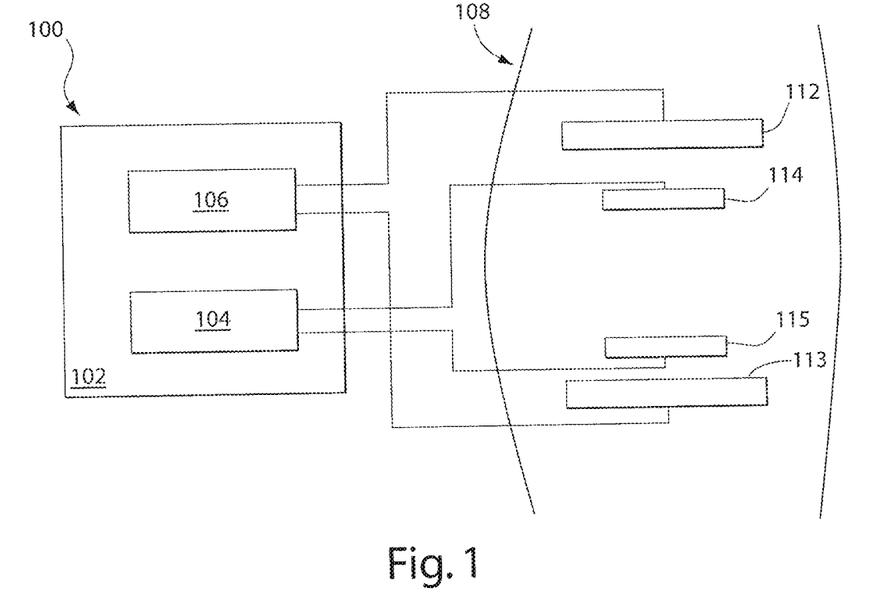
FIG. 1 is a diagram illustrating an example of a device that performs electrical impedance myography, according to one embodiment of the invention.

FIG. 1 illustrates an example of an apparatus 100 that may be used to perform multi-frequency EIM, according to one embodiment of the invention. Apparatus 100 includes electrodes 112-115, and also circuit 102 that measures and generates electrical signals using signal measurement circuit 104 and signal generation circuit 106. Apparatus 100 may include any components in any arrangement capable of delivering electrical signals and measuring electrical signals resulting from the electrical signals delivered, as the aspects of the invention are not limited in this respect.

In this embodiment, signal generating circuit 106 is coupled to two spaced-apart current-injecting electrodes 112 and 113, which may be applied to region of tissue 108. Using electrodes 112 and 113, an electrical signal is applied to region of tissue 108, for example, by passing an electrical current through the skin and into the region of tissue. The electrical signal that is applied may be any suitable signal, such as a predetermined voltage potential or a predetermined current. The electrodes may be isolated from a supply voltage using a transformer or any suitable device, such that a "floating" signal, and applied to the patient, thus enhancing the safety of the procedure.

In one example, the signal that is applied to current-injecting electrodes 112 and 113 may be a sinusoidally varying voltage having a magnitude of approximately 1 volt (peak-to-peak) and a frequency between 2 kilohertz and 2 megahertz. As a consequence of applying this signal, electric current is injected into region of tissue 108. However, it should be appreciated that these values of voltage, shape and frequency are provided merely by way of illustration, as the invention is not limited in these respects. Furthermore, any suitable circuit and/or technique may be used to generate the electrical signal applied to the region of tissue, as the aspects of the invention are not limited for use with any particular method of electrical signal generation and/or application.

Signal measuring circuit 104 is coupled to two spaced-apart voltage-measuring electrodes 114 and 115. While the generated signal is applied to tissue region 108 by signal generation circuit 106, signal measurement circuit 104 measures a signal at the tissue region using voltage-measuring electrodes 114 and 115. The signal that is measured may be a voltage difference between the two electrodes that results from the generated signal. Any suitable circuit and/or technique may be used to measure the signal, as the aspects of the invention are not limited in this respect.

Circuit 102 may analyze the measured signal and determine a characteristic of the region of tissue based on the measured signal. Any suitable property of the signal may be measured, such as the magnitude, phase, impedance, resistance and reactance or any suitable combination thereof. In some embodiments of the invention, the measured voltage difference at electrodes 114 and 115 may be divided by the current applied through electrodes 112 and 113 to obtain an impedance measurement. Circuit 102 may determine an impedance, resistance, reactance, phase and/or any other suitable property of the region. Based on the measured signal, any of suitable electrical parameters, and/or electrical properties of the region of tissue, circuit 102 may determine a muscle characteristic. For example, circuit 102 may diagnose and/or assess a neuromuscular disease based on any suitable criteria, as discussed in further detail below.

In some circumstances, circuit 102 may display one or more of the determined electrical parameters to facilitate diagnosis and/or assessment by a physician or technician. Circuit 102 may include any suitable components for performing such measurements, calculations, determinations and presentation functions. As one example, circuit 102 may include a lock-in amplifier for impedance measurement, a computer for performing calculations and a display for displaying the results to a human (e.g., a technician or a physician). However, it should be appreciated that any suitable components or combination of components may be used, as the invention is not limited for use with any particular components or configuration of the components.

Figure 2:
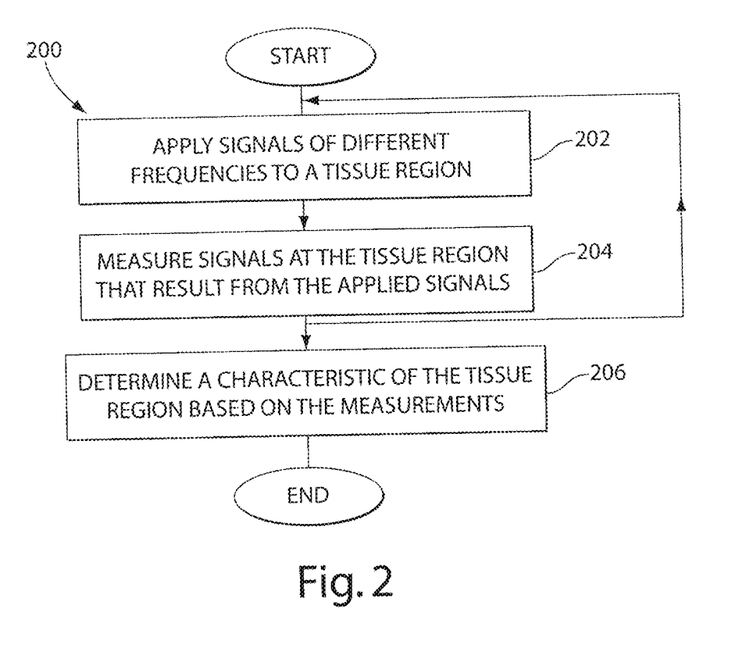
FIG. 2 is a flow chart illustrating a multi-frequency method of determining a characteristic of a tissue region of an organism, according to one embodiment of the invention.

FIG. 2 is a flowchart of a method 200 for performing multi-frequency EIM, according to one embodiment of the invention. As described above, a first signal of a first frequency is applied to a tissue region in step 202, and a first signal measurement is made in step 204, such that the measured signal is a result of applying the first signal of the first frequency. Next, a second signal of a second frequency is applied to the tissue region in step 202, and a second signal measurement is made for the second frequency in step 204. Further signals at different frequencies may also be applied, and corresponding measurements may be taken. Any suitable number of frequencies may be used in the multi-frequency EIM procedure, as the invention is not limited as to the number of frequencies measured or the exact frequencies at which measurements are taken. Preferably, if multi-frequency EIM is performed, the frequencies used should be of a number and value such that the measurements are sufficient to provide information useful in assessment or diagnosis of the tissue region, e.g., the assessment or diagnosis of a muscle condition.

In step 206, a characteristic of the region of tissue is determined based on the measurements. The characteristic that is determined may be a muscle characteristic, and may be determined based on one or more electrical properties obtained from the measurements, such as the impedance, phase, resistance and/or reactance of the muscle. As another example, a frequency-averaged impedance, phase, resistance and or reactance may be determined for at least a portion of the range of frequency measurement. The frequency-averaged parameter may be a useful parameter for comparing healthy vs. unhealthy tissue, and evaluating changes in the tissue over time. For example, a diagnosis of a neuromuscular condition may be made based on a frequency-averaged parameter being above or below a threshold value.

One or more electrical properties obtained from measurements taken from the region of tissue as a function of frequency may be used as a signature for the region of tissue. The term signature refers herein to any collection of information obtained from a region of tissue that is characteristic of the tissue. The signature of the tissue, once obtained, may be analyzed to assess, diagnose or otherwise determine a characteristic and/or condition of the region of tissue.

The signature of the tissue may be computationally processed and/or analyzed or presented to a physician or technician for analysis. As one example, a plot of an electrical parameter vs. frequency (e.g., resistance, reactance or phase of the tissue vs. frequency) may be displayed on a computer monitor, and a physician may make a diagnosis based on the plot displayed. Multiple plots displaying any of various electrical properties of the tissue with respect to frequency may be displayed, as the aspects of the invention are not limited in this respect.

Figure 3A:
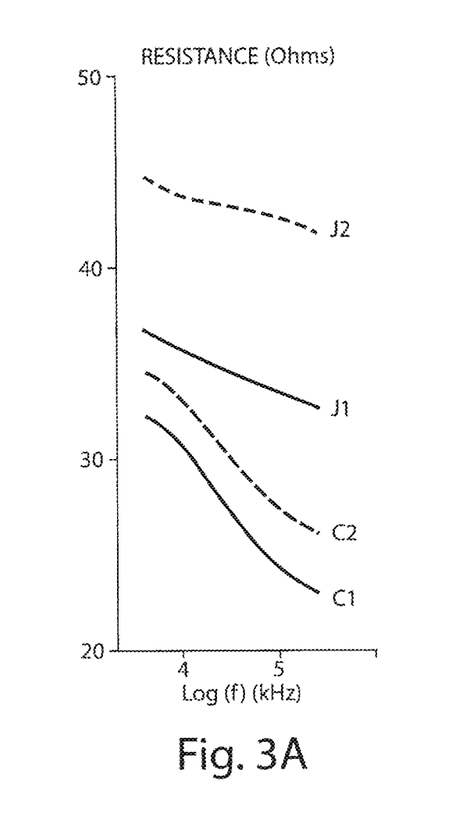
FIGS. 3A-C show plots of measured electrical parameters versus frequency, using multi-frequency electrical impedance myography obtained in accordance with various aspects of the invention.
Figure 3B:
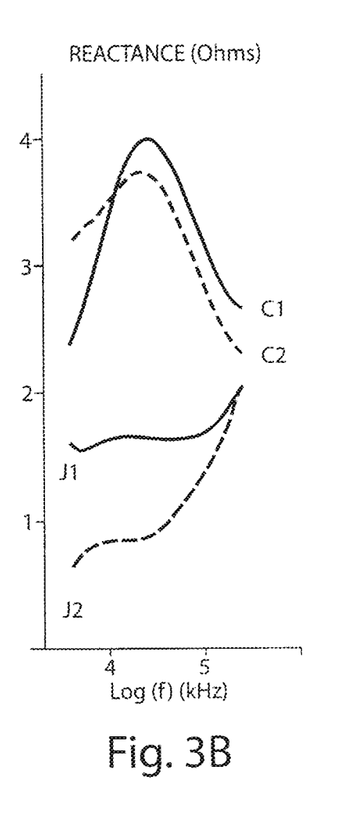
Figure 3C:
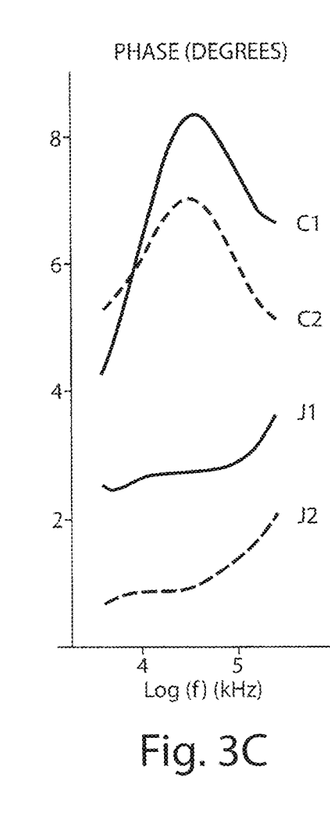

FIGS. 3A-C show plots of resistance, reactance and phase vs. the logarithm of frequency, respectively, measured for two different ALS patients (C and J) at two different visits, 3-4 months apart each. The solid line shows the measurements taken at the first visits and the dashed lines shows the measurements taken at the follow-up visits. Patient C had relatively mild ALS, while patient J had a more severe form of the disease. As can be readily appreciated from FIGS. 3B-C, the patient (J) with the more severe muscle disorder had lower phase and reactance values than the patient (C) with the less severe disorder. At the follow-up visit, both patients exhibited primarily a decrease in both phase and reactance measured, which illustrates the progression of the disease over time.

Additionally, the patient with less severe ALS had a much more pronounced frequency peak in both reactance and phase than the patient with the more severe form of ALS. These results are provided to illustrate various criteria that may be used in determining characteristics of a region of tissue using EIM, and which may displayed for use by a suitable medical practitioner. However, it should be appreciated that any suitable measured and/or calculated criteria may be used for characterization, as the invention is not limited as to the particular criteria used. In some circumstances, a diagnoses or assessment may be made by circuit 102. For example, circuit 102 may be configured to analyze the signature (e.g., one or more electrical properties as a function of frequency) to determine a characteristic of the region of tissue and/or to assess a condition of the region of tissue.

As discussed above, multidirectional (or rotational) EIM may be used for the assessment and characterization of a region of tissue. Multidirectional EIM can be performed by measuring the voltage difference between voltage-measuring electrodes that are arranged with a desired orientation with respect to an axis of the muscle fibers. Both the current-injecting electrodes and the voltage-recording electrodes may have the same orientation with respect to the muscle fibers. The electrical properties of the region of tissue at various orientations may be used to characterize the region of tissue, e.g., to assess a condition of the muscle and/or to perform a diagnosis of the muscle.

Figure 4A:
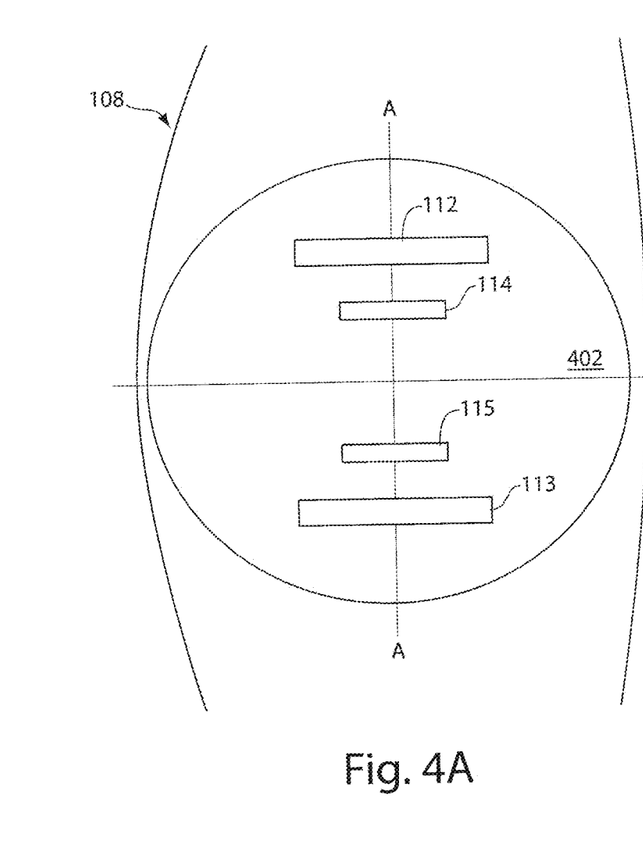
FIGS. 4A-B are diagrams illustrating an example of a device that performs rotational electrical impedance myography, according to one embodiment of the invention.
Figure 4B:
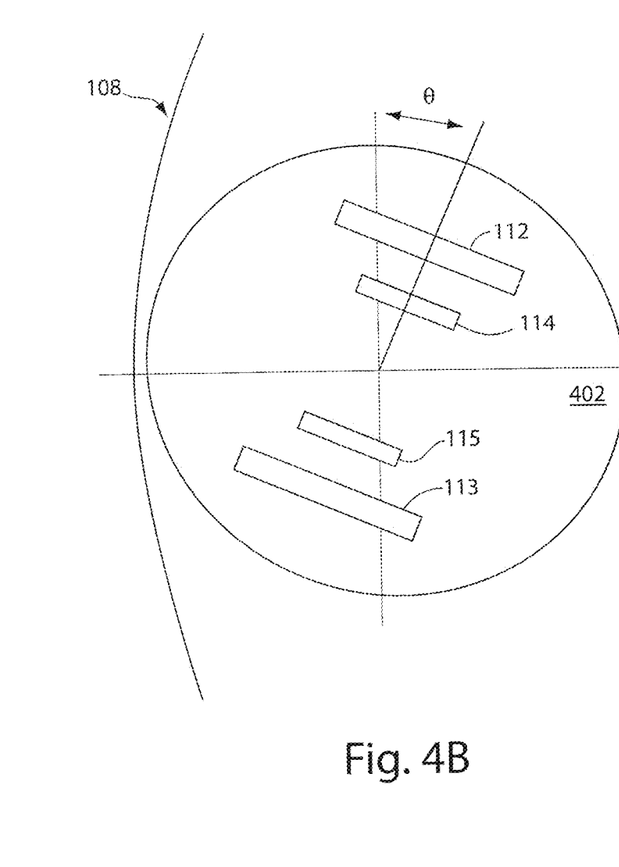

FIGS. 4A-B are diagrams illustrating performing EIM at different orientations with respect to a region of tissue 108. FIGS. 4A-B show electrodes 112-115, as described above with respect to FIG. 1. Electrodes 112-115 may be mounted on a base 402. FIG. 4A illustrates performing EIM along a direction A-A aligned with an axis of the region of tissue 108, e.g., substantially aligned with fibers of the muscle. FIG. 4B illustrates performing EIM along a direction at an angle θ with respect to the axis. Measurements obtained at the different orientations may be used to characterize and/or otherwise assess a condition of the region of tissue 108. Measurements may be obtained at multiple orientations to obtain information about how properties of the tissue vary with orientation (e.g., to determine a degree of anisotropy of the tissue), as discussed in further detail below.

In one embodiment, electrodes 112-115 are mounted on rotatable base 402, which is made of electrically insulating material. When a measurement is to be taken, electrodes 112-115 are brought into contact with the skin at the region of tissue, and are aligned in a first direction with respect to an axis of the region. When a second measurement is to be taken, base 402 is rotated by the desired angle θ, and electrodes 112-115 are again brought into contact with the skin at the new orientation.

Multiple different measurements may be made at different angles. As one example, measurements may be made at six different angles, each 30° apart (0°, 30°, 60°, 90°, 120° and) 150°. However, it should be appreciated that any suitable angle increments or number of measurements at different angles may be used, as the invention is not limited in this respect. Preferably, if rotational EIM is performed, the angles used should be of a number and increment such that the measurements are sufficient to provide information useful in assessment or diagnosis of the tissue region, e.g., the assessment or diagnosis of a muscle condition.

In another embodiment, electrodes 112-115 may be mounted on rotatable base 402 made of an electrically conductive material. In this embodiment, the electrically conductive base 402 may be brought into contact with the skin at the region of measurement, and the electrodes themselves may not contact the region directly. In one example, electrically conductive base 402 may be anisotropically conductive such that it preferentially conducts current in a direction perpendicular to the base (e.g., into the patient's body). The anisotropy of the conductive base can prevent undesirable cross-talk between the electrodes, and may allow current to penetrate a greater depth into the tissue region.

Figure 5:
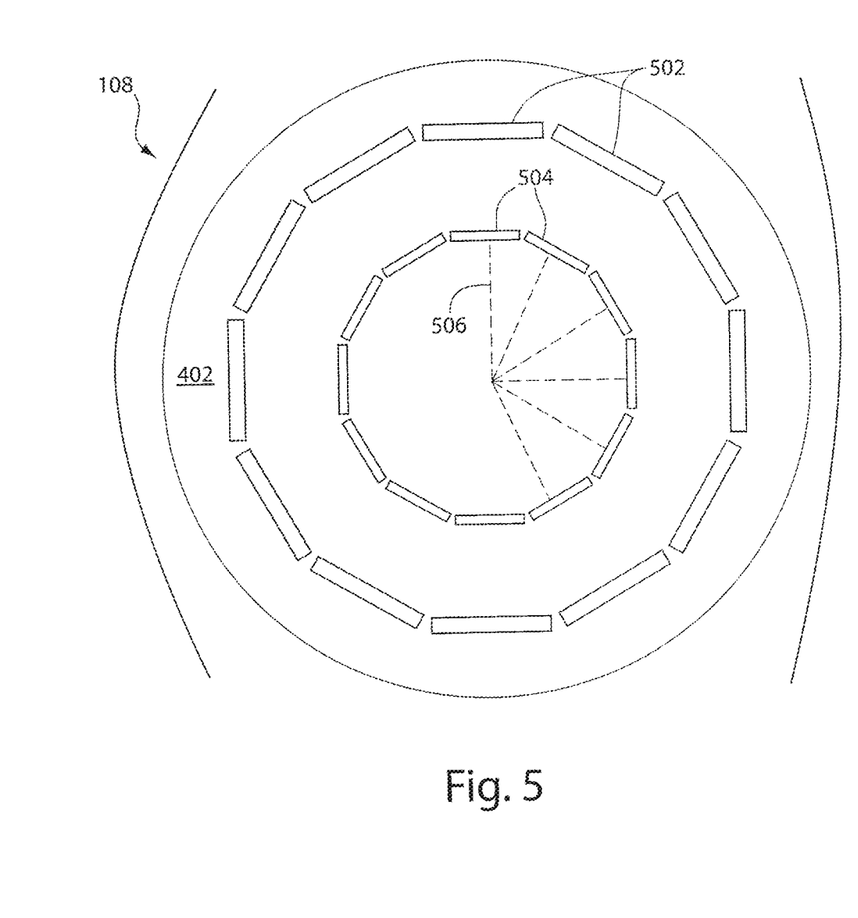
FIG. 5 is a diagram illustrating an example of a device that performs electrical impedance myography at a plurality of angles, according to one embodiment of the invention.

FIG. 5 illustrates another embodiment using rotational EIM, in which a plurality of current-injecting electrodes 502 and voltage-measuring electrodes 504 are mounted on base 402 at different orientations. Since the electrodes are mounted at a plurality of different orientations, it may not be necessary to rotate the electrodes or base 402 to make measurements at different angles. When a first measurement is to be made, an appropriate pair of current-injecting electrodes can be selected and coupled to signal-generating circuit 106 using any suitable switches. That is, the plurality of electrodes may be configured such that the combination of electrodes 502 and 504 at any desired orientation may be selectively activated.

For example, the current-injecting electrodes that lie along line 506 may be selected first. Additionally, the appropriate pair of voltage measuring electrodes 504 that lie along line 506 may be selected, and may be coupled to signal-measuring circuit 104 using any suitable switches. A first measurement may then be taken along direction 506. When a measurement is to be made along a different direction, the switches may be reconfigured to couple different electrodes 502 and 504 to the appropriate circuits, and measurement may be taken at a different orientation.

Figure 6:
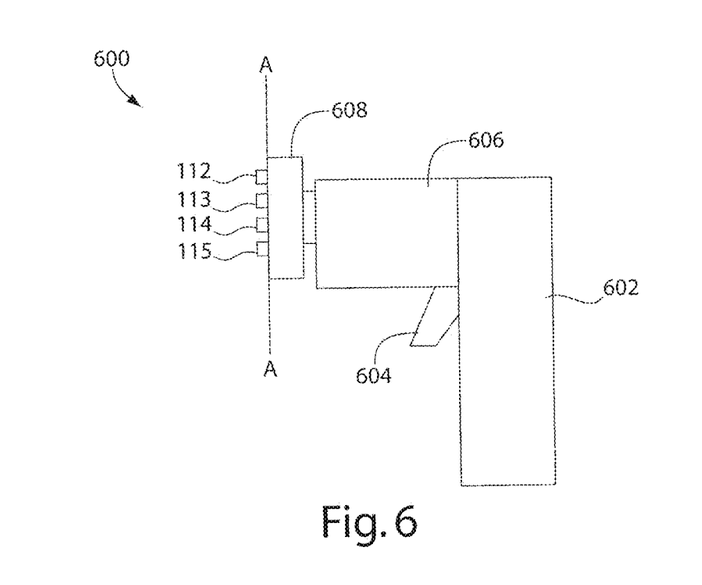
FIG. 6 is a diagram illustrating an example of a hand-held device that performs electrical impedance myography, according to one embodiment of the invention.

FIG. 6 illustrates an example of a hand-held apparatus 600 that may be used for performing EIM, including rotational and/or multi-frequency EIM. Providing a hand-held EIM device may facilitate making EIM measurements, and thus may reduce the amount of time needed to make the measurements. Hand-held apparatus 600 may include a handle 602, a user interface 604, a body 606, base 608 and electrodes 112-115. The electrodes may be coupled to circuit 102 in any suitable way, such as through a cord attached at the bottom of handle 602, for example. FIG. 6 illustrates direction A-A corresponding to direction A-A illustrated in FIG. 4A.

In one embodiment, base 608 may be rotatable, as discussed above, for performing rotational EIM. In another embodiment, base 608 may not be rotatable, but may have a plurality of electrodes 502 and 504 positioned at different orientations, as described in connection with FIG. 5. Apparatus 600 may be configured such that either technique may be used, depending on the type of base/electrode combination that is mounted to the apparatus. In some circumstances, it may be desirable to provide multiple different base/electrode combinations of different sizes that may be easily interchangeable for measuring different types of muscles, or muscles of different sizes. When a different size is needed, the base 608 may be detached from apparatus 600 and another base may be attached.

Figure 7:
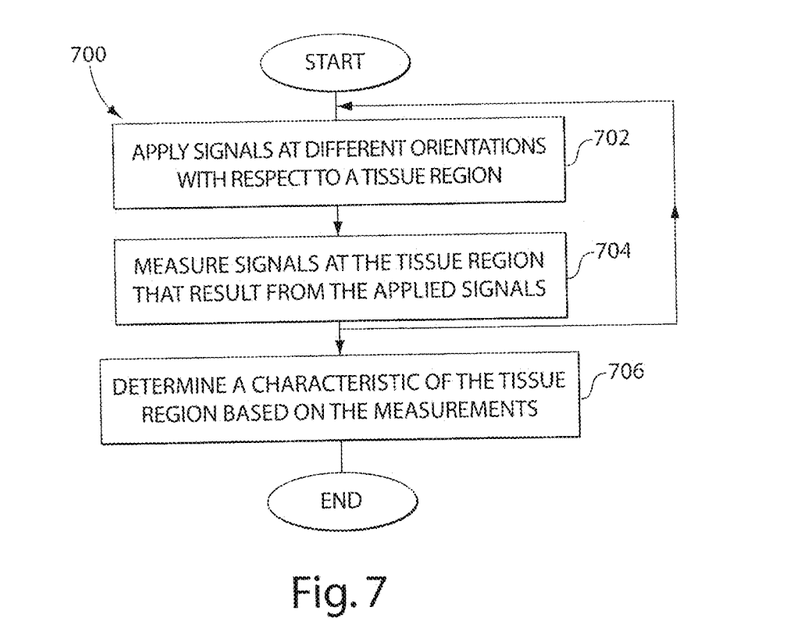
FIG. 7 is a flow chard illustrating a method of performing rotational electrical impedance myography, according to one embodiment of the invention.

FIG. 7 is a flow chart of a method 700 of performing rotational EIM, according to one embodiment of the invention. In step 702, a first signal is applied to a tissue region at a first orientation, and in step 704 a second signal, resulting from the first applied signal, is measured at the region. Next, a third signal is applied to the tissue region at a different orientation. For example, a linear electrode array may be rotated, and another measurement may be made, as illustrated in FIGS. 4A-B. As another example, if a quasi-circular electrode array is used (FIG. 5), a different set of electrodes may be selected that correspond to a different orientation, and a corresponding measurement may be made. It is preferred that at least one measurement be made along a muscle axis, and that at least one measurement be made perpendicular to the muscle axis. Finally, in step 706, a tissue characteristic is determined based on the measurements, using any suitable criteria as discussed above.

The one or more electrical properties obtained as a function of orientation may be used as a signature of the region of tissue. As discussed above, this signature may be analyzed to determine a characteristic of the tissue and/or to assess a condition of the muscle. For example, how the one or more electrical properties vary with orientation (e.g., a degree of anisotropy) may be used to assess the health of the tissue and/or diagnose a condition such as a specific neuromuscular disorder. The signature may be analyzed quantitatively, or compared to a reference signature obtained from known healthy or diseased tissue to assist in the analysis and/or diagnosis of the tissue.

Figure 8A:
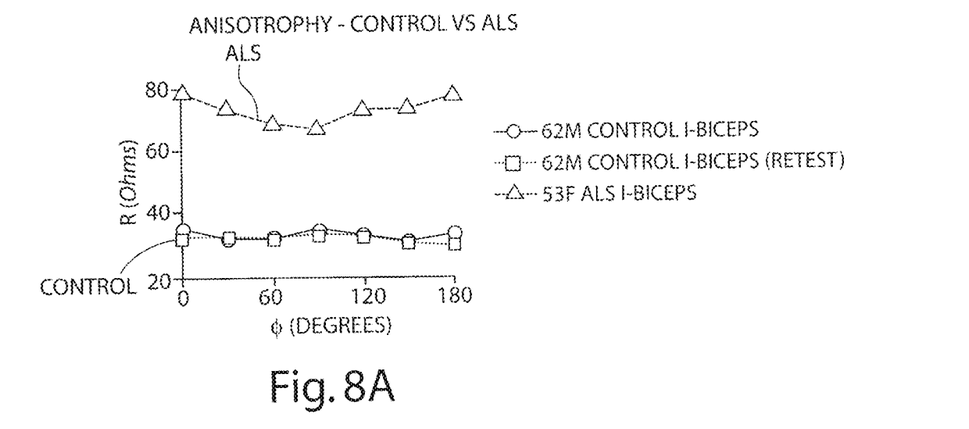
FIGS. 8A-C show plots of measured electrical parameters versus angular orientation of the measurement obtained in accordance with various aspects of the invention.
Figure 8B:
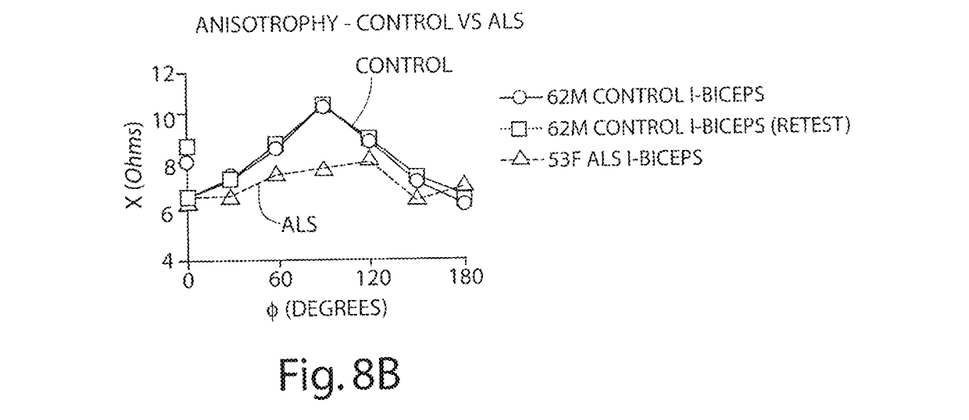
Figure 8C:
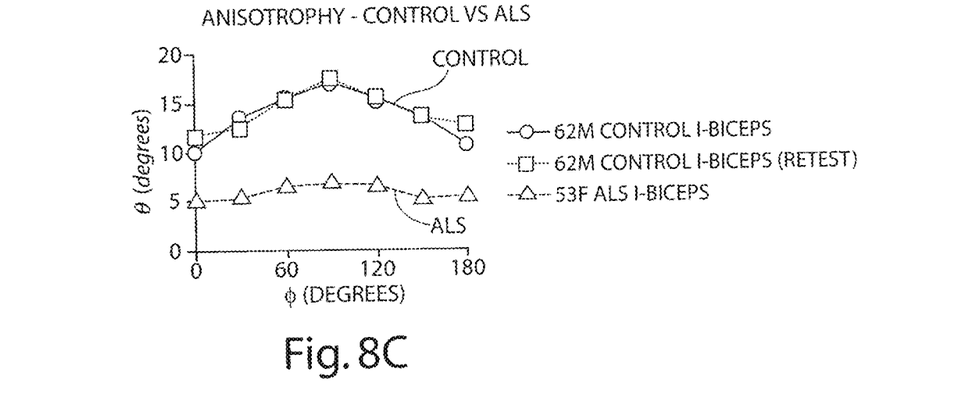

FIGS. 8A-C show plots of resistance, reactance and phase vs. angular orientation, respectively, for both control patients and an ALS patient. As shown in the figures, the measured electrical parameters depend on the orientation of the measurement with respect to an axis of the muscle fibers, with 0° being aligned with the axis. The reactance and phase were lower for the patient with ALS than for the control patients. Additionally, the control measurements exhibited more significant peaks at 90° in both reactance and phase for the control patients than for the patient with ALS. These and/or any other suitable criteria may be used in determining a characteristic of a region of tissue, as these examples are described merely by way of illustration.

In one embodiment, the frequency dependence and orientation dependence of one or more electrical properties of a region of tissue are both exploited to obtain a signature of the region of tissue. For example, at each of a plurality of orientations, an electrical signal may be applied at a plurality of frequencies. Measurements of the tissue may be taken for each frequency at each orientation to determine one or more electrical properties of the tissue at the various frequencies and orientations. By obtaining information about both frequency and orientation dependence, a richer set of indicators are available to facilitate determining a muscle characteristic and/or assessing a condition of the tissue.

Figure 9:
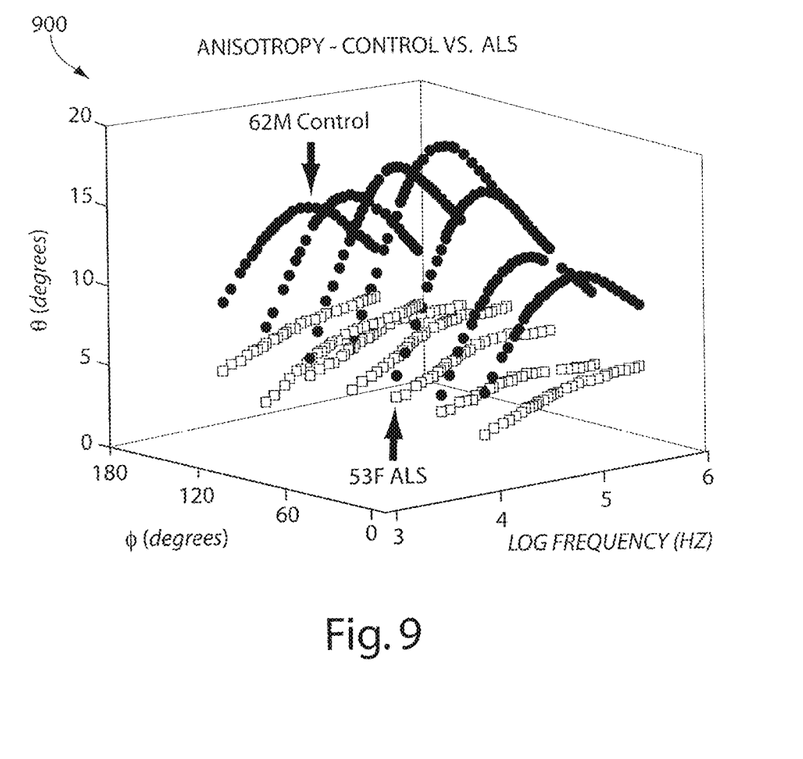
FIG. 9 is a three-dimensional plot of measured electrical parameters versus frequency and angular orientation obtained in accordance with various aspects of the invention.

FIG. 9 shows a three-dimensional plot 900 illustrating the results of performing both multi-frequency and rotational EIM. Overall, the control patient exhibited higher phase measurements and more pronounced phase peaks with respect to both frequency and orientation, as compared to a patient with ALS. Thus, multi-frequency and rotational EIM can be useful, either alone and in combination, for assessing and detecting neuromuscular disorders. In particular, the quantitative nature of the measurements may allow for more accurate assessment and diagnoses of neuromuscular disorders, and also the evaluation of therapies for muscle disorders.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. The invention is capable of other embodiments and of being practiced or of being carried out in various ways. In particular, various EIM techniques described herein may be used alone or in any combination.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A device adapted for application to a surface of skin to assess a region of muscle tissue, the device comprising:
   a first electrode adapted to apply an electrical current signal to the region of muscle tissue;
   a second electrode adapted to detect an electrical voltage signal at the region of muscle tissue resulting from the application of the electrical current signal;
   a rotatable base on which the first electrode and the second electrode are mounted and arranged such that, when the rotatable base is rotated, the first electrode and the second electrode are rotated with respect to the region of muscle tissue to apply the electrical current signal to the region of muscle tissue at a plurality of orientations so as to propagate through at least a portion of the region of muscle tissue in a respectively different direction with respect to a first axis, the first axis being aligned with fibers of a muscle in the region of muscle tissue, and to detect the electrical voltage signal resulting from the application of the electrical current signal at the plurality of orientations;
   a body, wherein the rotatable base is mechanically attached to the body and configured to rotate with respect to the body;
   a handle coupled to the body at a location opposite the rotatable base; and circuitry coupled to the second electrode and configured to obtain at least one measurement indicative of the electrical voltage signal at each of the plurality of orientations, determine at least one electrical property of the region of muscle tissue at each orientation of the plurality of orientations, and assess a condition of the region of muscle tissue based, at least in part, on the at least one electrical property, by comparing the at least one electrical property with a signature of the muscle tissue.

2. The device of claim 1, wherein the first electrode and the second electrode are spaced apart in a first direction such that the electrical current signal applied to the region of muscle tissue propagates essentially in the first axis through the region of muscle tissue toward the second electrode.

3. The device of claim 2, wherein, when the rotatable base is rotated, the electrical current signal propagates in a different direction through the region of muscle tissue with respect to the first axis of the region of muscle tissue at each of the plurality of orientations.

4. The device of claim 3, wherein the rotatable base is capable of being rotated through a range of at least 90°.

5. The device of claim 3, wherein the rotatable base is capable of being rotated through a range of at least 180°.

6. The device of claim 3, wherein the rotatable base is capable of being rotated through a range of at least 360°.

7. The device of claim 3, wherein the circuitry is adapted to determine at least one property based on the at least one measurement to generate a first signature, the first signature comprising the at least one property as a function of orientation.

8. The device of claim 1, wherein the first electrode is adapted to apply a plurality of electrical current signals to the region of muscle tissue, each of the plurality of electrical current signals having a respective one of a plurality of frequencies, and wherein the second electrode is adapted to detect a plurality of electrical voltage signals, each of the plurality of electrical voltage signals resulting from a respective one of the plurality of electrical current signals.

9. The device of claim 8, wherein the circuitry is adapted to obtain a plurality of measurements, each of the plurality of measurements indicative of a respective one of the plurality of electrical voltage signals.

10. The device of claim 9, wherein the circuitry is adapted to determine at least one property based on each of the plurality of measurements to generate a first signature, the first signature comprising the at least one property as a function of orientation and frequency.

11. The device of claim 10, wherein the at least one property includes a resistance of the region of muscle tissue at the respective orientation and frequency.

12. The device of claim 10, wherein the at least one property includes a reactance of the region of muscle tissue at the respective orientation and frequency.

13. The device of claim 10, wherein the at least one property includes a phase derived from a resistance and a reactance of the region of muscle tissue at the respective orientation and frequency.

14. The device of claim 7, wherein the circuitry is further configured to determine a degree of anisotropy of the first signature.

15. The device of claim 10, wherein the circuitry is further coupled to receive the first signature and adapted to compare the first signature with a second signature obtained from a reference region of tissue.

16. The device of claim 7, further comprising a display coupled to the circuitry, the display adapted to present the first signature in a human perceptible format.

17. The device of claim 1, wherein the base is detachably coupled to the body.

18. The device of claim 1, wherein the base is formed of an electrically conductive material and is configured to conduct current in a direction perpendicular to the base.

19. The device of claim 1, wherein the body is mechanically coupled to a side of the rotatable base opposite a side on which the first electrode and the second electrode are mounted and arranged.

* * * * *